US009223931B2

(12) United States Patent
Kim et al.

(10) Patent No.: US 9,223,931 B2
(45) Date of Patent: Dec. 29, 2015

(54) ULTRASOUND DIAGNOSTIC DEVICE AND METHOD OF DISPLAYING ULTRASOUND IMAGES

(75) Inventors: Sung Yun Kim, Seoul (KR); Yun Jin Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 1024 days.

(21) Appl. No.: 12/343,352

(22) Filed: Dec. 23, 2008

(65) Prior Publication Data

US 2009/0171209 A1  Jul. 2, 2009

(30) Foreign Application Priority Data

Dec. 27, 2007  (KR) .................. 10-2007-0138414

(51) Int. Cl.
*A61B 8/00* (2006.01)
*G06F 19/00* (2011.01)

(52) U.S. Cl.
CPC ............... *G06F 19/321* (2013.01); *A61B 8/00* (2013.01); *G06F 19/3406* (2013.01)

(58) Field of Classification Search
CPC ........................... G06F 19/321; G06F 19/3406
USPC .......................................... 600/407, 437–475
See application file for complete search history.

(56) References Cited

U.S. PATENT DOCUMENTS

| 6,139,497 | A | 10/2000 | Amemiya et al. |
| 6,217,515 | B1 | 4/2001 | Yamakawa et al. |
| 6,331,776 | B1 | 12/2001 | Debbins et al. |
| 6,620,102 | B2 * | 9/2003 | Miwa et al. .................. 600/443 |
| 7,006,862 | B2 * | 2/2006 | Kaufman et al. ............. 600/523 |
| 8,175,347 | B2 | 5/2012 | Hirakawa |
| 2002/0156374 | A1 | 10/2002 | Miwa et al. |
| 2003/0016782 | A1 | 1/2003 | Kaufman et al. |
| 2004/0225219 | A1 * | 11/2004 | Demers ......................... 600/443 |
| 2005/0096539 | A1 * | 5/2005 | Leibig et al. .................. 600/437 |
| 2005/0131293 | A1 | 6/2005 | Kato |

(Continued)

FOREIGN PATENT DOCUMENTS

| EP | 1 465 196 A1 | 10/2004 |
| EP | 1 557 837 A1 | 7/2005 |

(Continued)

OTHER PUBLICATIONS

Korean Office Action issued in Korean Patent Application No. KR 10-2007-0138414 dated Sep. 16, 2011.

(Continued)

*Primary Examiner* — Mark Remaly
(74) *Attorney, Agent, or Firm* — McDermott Will & Emery LLP

(57) ABSTRACT

The present invention relates to an ultrasound diagnostic device. The ultrasound diagnostic device comprises: a storage unit configured to store a plurality of consecutive image frames based on ultrasound echoes reflected from a target object; an image processing unit configured to form preview images of the image frames, wherein the preview images are stored in the storage unit in association with the corresponding image frames; and a user input unit allowing a user to input a selection instruction for selecting one of the preview images, wherein the image processing unit is further configured to read out an image frame corresponding to the selected preview image from the storage unit in response to the selection instruction.

10 Claims, 3 Drawing Sheets

(56) References Cited

U.S. PATENT DOCUMENTS

| | | | |
|---|---|---|---|
| 2005/0171430 A1* | 8/2005 | Zhang et al. | 600/437 |
| 2006/0058625 A1 | 3/2006 | Mori | |
| 2006/0176958 A1* | 8/2006 | Babonneau et al. | 375/240.19 |
| 2007/0161895 A1 | 7/2007 | Kim et al. | |
| 2007/0242069 A1 | 10/2007 | Matsue et al. | |
| 2007/0287916 A1 | 12/2007 | Kim et al. | |
| 2013/0289405 A1 | 10/2013 | Wang et al. | |

FOREIGN PATENT DOCUMENTS

| | | | |
|---|---|---|---|
| JP | 2000060848 A | 2/2000 | |
| JP | 2003126087 A | 5/2003 | |
| JP | 2004008350 A | 1/2004 | |
| JP | 2004057356 A | 2/2004 | |
| JP | 2004-180940 A | 7/2004 | |
| JP | 2005-173897 A | 6/2005 | |
| JP | 2005168807 A | 6/2005 | |
| JP | 2005245961 A | 9/2005 | |
| JP | 2006014989 A | 1/2006 | |
| JP | 2006-060611 A | 3/2006 | |
| JP | 2006-061626 A | 3/2006 | |
| JP | 2006075513 A | 3/2006 | |
| JP | 2006-087653 A | 4/2006 | |
| JP | 2006-141508 A | 6/2006 | |
| JP | 2006-280792 A | 10/2006 | |
| JP | 2006325995 A | 12/2006 | |
| JP | 2007029458 A | 2/2007 | |
| JP | 2007-143648 A | 6/2007 | |
| KR | 1999-007087 | 1/1999 | |
| KR | 2000-0022899 A | 4/2000 | |
| KR | 10-2007-0009273 A | 1/2007 | |
| KR | 10-0850347 B1 | 7/2008 | |
| WO | 2005117711 A2 | 12/2005 | |

OTHER PUBLICATIONS

Partial European Search Report issued in European Patent Application No. EP 08022080.9 dated Jun. 4, 2013.

Japanes Office Action issued in Application No. 2008-329061 dated Aug. 27, 2013.

Extended European Search Report issued in Application No. 08022080.9 dated Sep. 30, 2013.

Japanese Final Rejection, w/ English translation thereof, issued in Japanese Patent Application No. JP 2008-329061 dated Jan. 21, 2014.

Japanese Office Action issued in Japanese Application No. 2014-105687 dated May 12, 2015, with English Translation.

Japanese Appeal Decision issued in Japanese Application No. 2008-329061 dated Aug. 25, 2015, with English Translation.

* cited by examiner

ULTRASOUND DIAGNOSTIC DEVICE AND METHOD OF DISPLAYING ULTRASOUND IMAGES

The present application claims priority from Korean Patent Application No. 10-2007-0138414 filed on Dec. 27, 2007, the entire subject matter of which is incorporated herein by reference.

BACKGROUND OF THE INVENTION

1. Technical Field

The present invention generally relates to ultrasound diagnostic apparatuses, and more particularly to an ultrasound diagnostic apparatus and a method of displaying ultrasound images.

2. Background Art

An ultrasound diagnostic apparatus has become an important and popular diagnostic tool due to its non-invasive and non-destructive nature. Modern high-performance ultrasound imaging diagnostic devices and techniques are commonly used to produce two- or three-dimensional images of internal features of patients. The ultrasound diagnostic apparatus may provide the ultrasound images in various image display modes. The image display modes may include a real-time display mode, a freeze mode and a cine replay mode.

When in the real-time display mode, the ultrasound diagnostic apparatus may transmit and receive ultrasound signals to obtain ultrasound image data. The ultrasound diagnostic apparatus may display an ultrasound image of a target object in real time based on the ultrasound image data. In such a case, while displaying the ultrasound image, the ultrasound image data, which include a plurality of image frames, may be also stored in a storage such as a cine memory. When the image frames are stored, indices may be assigned thereto. The indices may be assigned according to the acquisition time of the image frames.

If the freeze mode is set, then the conventional ultrasound diagnostic apparatus may stop transmitting the ultrasound signals to the target object and provide the indices of the image frames stored in the storage. If a user selects one of the indices by using an input device such as a mouse, a keyboard or a track ball, then an image frame corresponding to the selected index may be read out from the storage and then displayed on a display unit. In such a case, since the user has to select the indices one by one to display a desirable image frame, the user may feel inconvenient when searching for the desirable image frame.

If the cine replay mode is set in the conventional ultrasound diagnostic apparatus, then the image frames stored in the storage may be read out in the order (or in the inverse order) of the acquisition times. A cine image may be replayed based on the read-out image frames. Also, the ultrasound diagnostic apparatus may provide indices on a screen of the display unit in the cine replay mode. The user may select an index corresponding to a start image frame of the cine image to be replayed and an index corresponding to an end image frame of the cine image to be replayed. The conventional ultrasound diagnostic apparatus merely sets a replay period by selecting indices corresponding to the start image frame and the end image frame of the cine image. Thus, the cine image for only one replay period may be displayed.

DETAILED DESCRIPTION OF THE INVENTION

Figure 1:
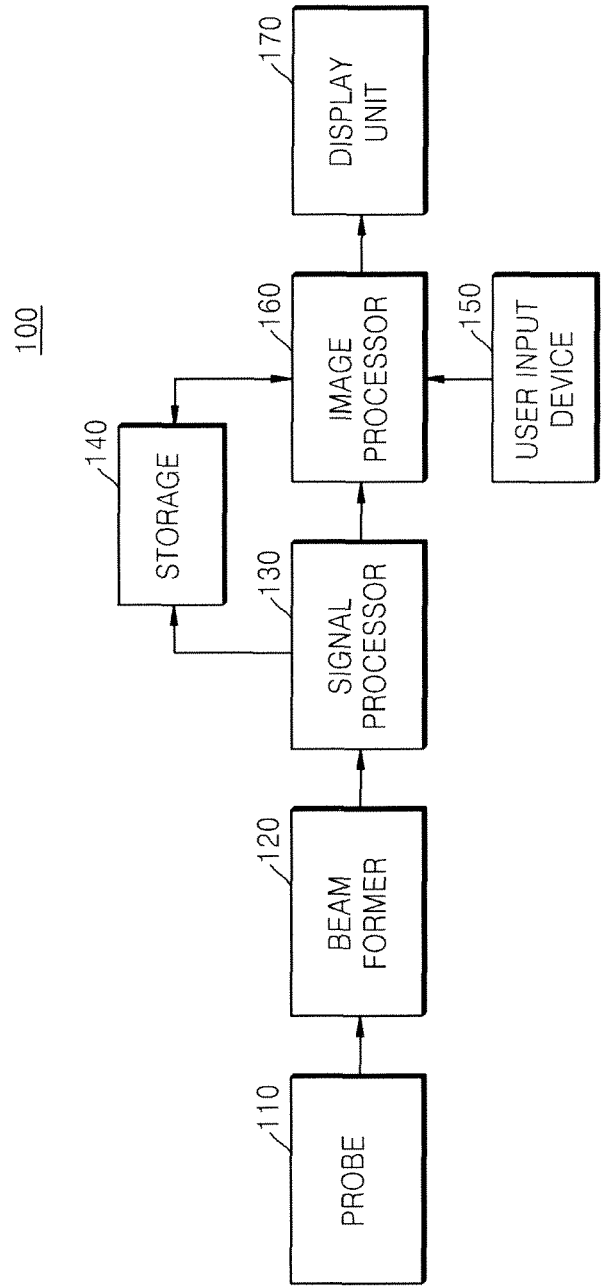
FIG. 1 is a block diagram showing an embodiment of an ultrasound diagnostic apparatus.

FIG. 1 is a block diagram showing an embodiment of an ultrasound diagnostic apparatus. Referring to FIG. 1, the ultrasound diagnostic apparatus 100 may include a probe 110 for transmitting and receiving ultrasound signals. The probe 110 may include at least one transducer element configured to generate ultrasound signals in response to transmit pulse signals produced from transmit pulsers (not shown). The ultrasound signals may be transmitted to a target object. The probe 110 may convert ultrasound echoes reflected from the target object into electrical receive signals.

The probe 110 may be coupled to a beam former 120, which may apply delays to the transmit pulse signals to form a transmit pattern such that the ultrasound signals generated from the elements are focused on scan lines. Also, the beam former 120 may be configured to apply delays to the receive signals in consideration of distances between the elements and focal points and sum the delayed receive signals, thereby forming a receive-focused beam.

The ultrasound diagnostic apparatus 100 may further include a signal processor 130 configured to perform signal processing upon the receive-focused beam to thereby form cine data. The cine data may be constructed with a plurality of frames. The ultrasound diagnostic apparatus 100 may further include a storage 140. The cine data may be stored in the storage 140.

The ultrasound diagnostic apparatus 100 may include a user device 150 allowing the user to input selection instructions for selecting one of image display modes of the ultrasound diagnostic apparatus 100. The user device 1550 may be an arbitrary input device such as a mouse, a keyboard, a trackball and the like. The image display modes may include a real-time display mode, a freeze mode, a cine replay mode and the like. Also, the user device 150 may further allow the user to input a bookmark setting instruction for setting bookmarks to numerous frames of the cine data stored in the storage 140.

The ultrasound diagnostic apparatus 100 may further include an image processor 160 configured to perform image processing upon the cine data to thereby form ultrasound image signals. The image processor 160 may scan convert the cine data and render the scan-converted data to thereby form the ultrasound image signals. The image processor 160 may further form preview images corresponding to the respective frames of the cine data. The preview images may be formed in smaller sizes than the frames. Further, the preview images may be linked to the corresponding frames and stored in the storage 140.

In one embodiment, the image processor 160 may be configured to set a mark to a frame whose data value steeply varies among the frames. For example, the image processor 160 may compute mean deviation of each frame and set the mark to a frame whose mean deviation varies over a threshold value. Also, the image processor 160 may be configured to set a mark to a frame obtained when a view mode is changed. In such a case, the image processor 160 may form preview images only for the frames with the marks set. The frames may be stored in the storage 140 in association with the preview images.

In one embodiment, the image processor 160 may set bookmarks in response to the bookmark setting instruction inputted through the user device 150. The bookmarks may be set to first and last frames of a cine image to be replayed. A plurality of replay periods may be set through a plurality of bookmarks. Bookmark information may include information of frames to be replayed. The bookmark information may be indicated at the preview images displayed on the display unit 170. If the bookmark setting instruction is not inputted from the user device 150, then the bookmarks may be set at a constant interval. The display unit 170 may receive the ultrasound image signals from the image processor 160 to thereby display an ultrasound image of the target object.

Hereinafter, an operation of the ultrasound diagnostic apparatus 100 will be described below for the real-time display mode, the freeze mode and the cine replay mode. If the real-time display mode is set, then the image processor 160 may directly receive cine data from the signal processor 130 and perform image processing thereupon to thereby form the ultrasound image signals. The display unit 170 may display the ultrasound image of the target object in real time based on the ultrasound image signals.

Figure 2:
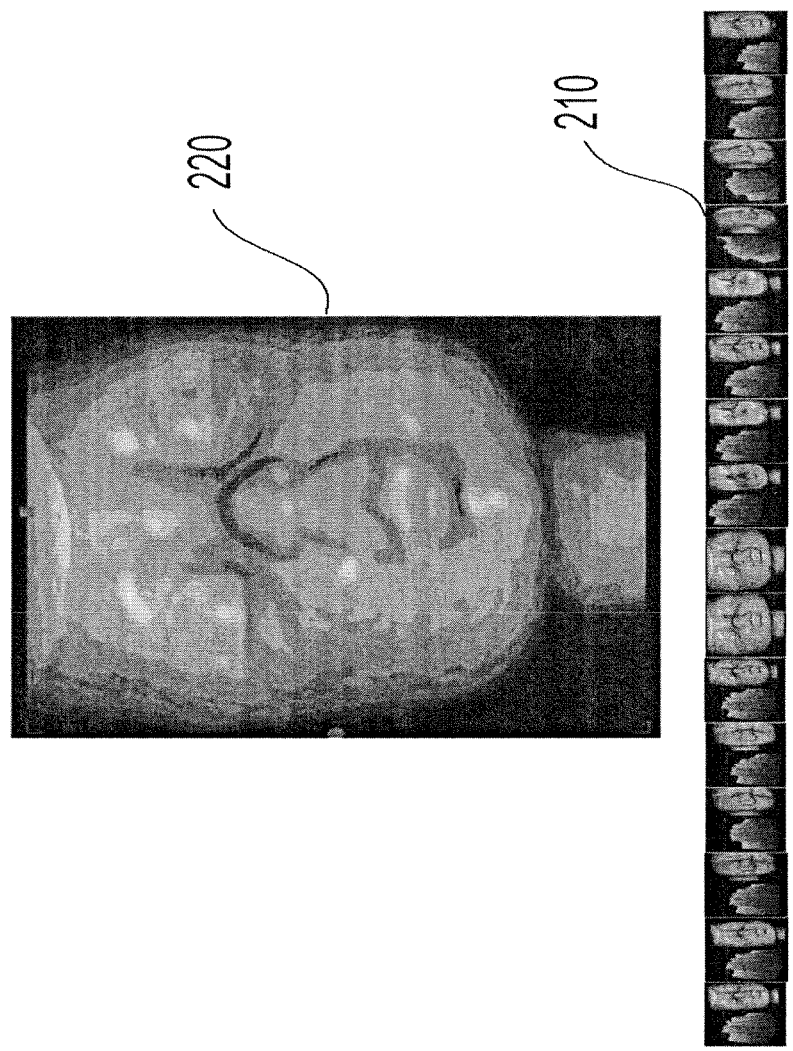
FIG. 2 is an exemplary diagram showing an example of displaying a plurality of preview images and a selected image frame.

If the freeze mode is set from the real-time display mode, then the image processor 150 may stop receiving the cine data from the signal processor 130 and read out preview images from the storage 140. The read-out preview images may be transmitted to the display unit 140 so that the preview images 210 may be displayed at a predetermined position on a screen of the display unit 140, as shown in FIG. 2. Also, the image processor may read out preview images, on which the marks are set based on the instructions inputted from the user device 150 for display on the display unit 170.

If a selection instruction for selecting one of the preview images displayed on the display unit 160 is inputted from the user device 150, then the image processor 140 may read out frame data corresponding to the selected preview image and perform image processing upon the read-out frame data to thereby form a frame image signal. The display unit 170 may display a frame image 220 based on the frame image signal, as shown in FIG. 2. In such a case, the frame image 220 may be displayed together with the preview images 210. Since the user can easily select a desirable frame image through the preview images 210, an operation time of the ultrasound diagnostic apparatus may be reduced.

Figure 3:
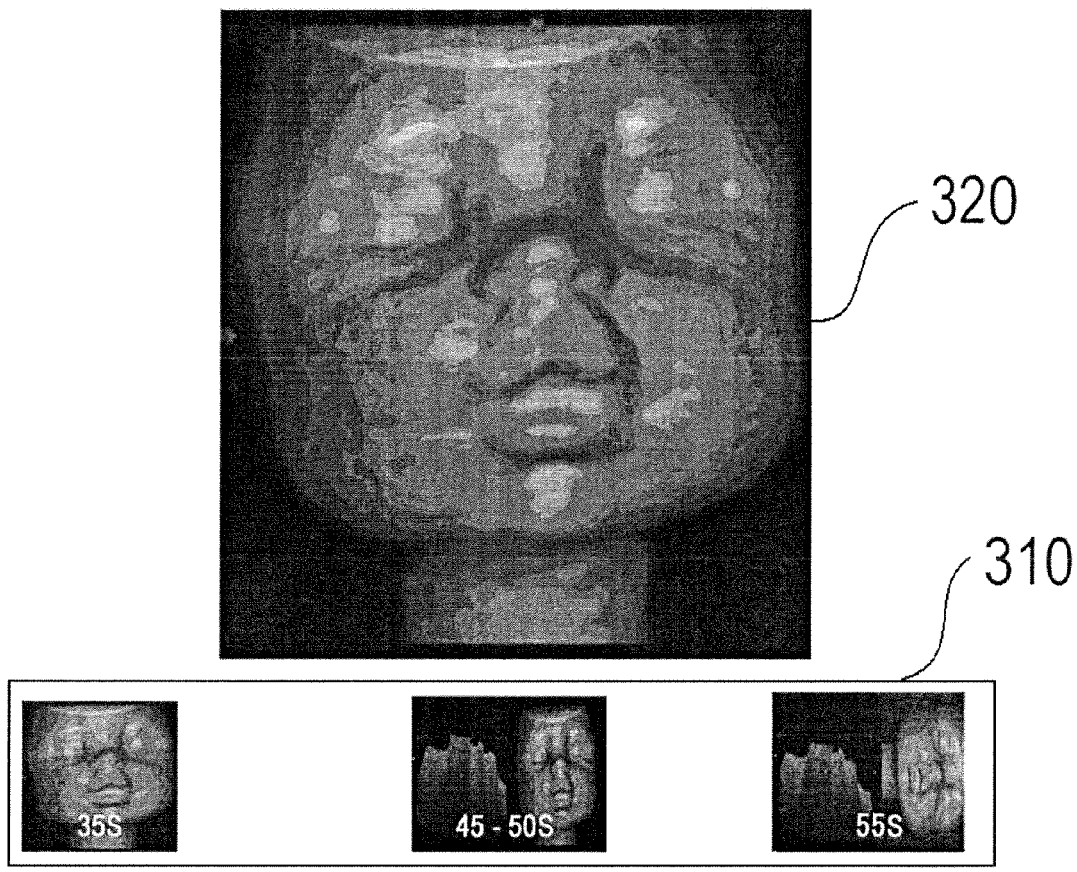
FIG. 3 is an exemplary diagram showing an example of displaying a plurality of preview images with bookmarks set and a selected cine image.

Further, if the cine replay mode is set in response to the instruction inputted from the user device 150, then the image processor 140 may read out preview images 310, on which the bookmarks are set, among the preview images stored in the storage 140. The read-out preview images may be displayed on the display unit 170, as shown in FIG. 3. If the user selects one of the preview images displayed on the screen of the display unit 170, then the image processor 160 may read out frame data based on frame information included in the bookmark information. The image processor 160 may be configured to perform image processing upon the frame data to thereby form a cine image. The cine image 320 may be displayed on the display unit 170, as shown in FIG. 3.

It is described that the preview images may be formed for the frames obtained in the real-time display mode and stored together with the cine data in the storage 140 in one embodiment. However, it should be noted herein that the preview images may be formed based on frames constructing the cine data, which are stored in the storage 140, when the freeze mode or the cine replay mode is set.

As mentioned above, since the preview images for the frames stored in the cine memory are provided, the user may easily select a desirable frame. Thus, an operation time of the ultrasound diagnostic apparatus may be reduced. Also, since the plurality of bookmarks may be set to the frames, a plurality of cine images may be replayed.

In accordance with one aspect of the present invention, there is provided an ultrasound diagnostic apparatus, comprising: a storage configured to store a plurality of consecutive image frames based on ultrasound echoes reflected from a target object; an image processor configured to form preview images of the image frames, wherein the preview images are stored in the storage in association with the corresponding image frames; and a user device allowing a user to input a selection instruction for selecting one of the preview images, wherein the image processor is further configured to read out an image frame corresponding to the selected preview image from the storage in response to the selection instruction.

In accordance with another aspect of the present invention, there is provided a method of displaying an ultrasound image, comprising: a) storing a plurality of consecutive image frames based on ultrasound echoes reflected from a target object; b) forming preview images of the image frames; c) receiving a selection instruction for selecting one of the preview images; and d) reading out an image frame corresponding to the selected preview image in response to the selection instruction.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound diagnostic apparatus, comprising:
a storage implemented in the ultrasound diagnostic apparatus, the storage configured to store cine data constructed with a plurality of consecutive image frames based on signal processing upon ultrasound echoes from a target object if a real-time display mode is set;
an image processor implemented in the ultrasound diagnostic apparatus and coupled to the storage, the image processor configured to set a plurality of marks to a plurality of image frames among the consecutive image frames, and read the storage to form preview images of the image frames with the marks set, wherein the preview images are formed in smaller sizes than the image frames, and the preview images are linked to the corresponding image frames and stored in the storage in association with the corresponding image frames;

a display implemented in the ultrasound diagnostic apparatus and coupled to the image processor, the display configured to display at least one preview image among the preview images at a predetermined position on a screen of the display; and a user input device implemented in the ultrasound diagnostic apparatus, the user input device coupled to the image processor and configured to receive a bookmark setting instruction from a user, wherein the image processor is further configured to set bookmarks to a first frame and a last frame of a cine image to be replayed among the consecutive image frames in response to the bookmark setting instruction, and if a freeze mode is set from the real-time display mode in response to an instruction inputted from the user input device, the image processor may read out the preview images on which the marks are set and display the read-out preview images, and when the user input device receives a user input for selecting one of the read-out preview images, on which the marks are set, displayed on the display, the image processor reads out frame data corresponding to the selected preview image and performs image processing upon the read-out frame data to thereby form a frame image signal, and the display further displays a frame image based on the frame image signal, if a cine replay mode is set from the real-time display mode in response to an instruction inputted from the user input device, the image processor may read out preview images on which the bookmarks are set among the preview images on which the marks are set and display the read-out preview images, bookmark information including information of the first frame and the last frame of the cine image is indicated at the read-out preview images displayed on the display, when the user input device receives a user input for selecting one of the read-out preview images, on which the bookmarks are set, displayed on the display, the image processor reads out the frames of the cine image based on the bookmark information and performs image processing upon the frames of the cine image to thereby form the cine image, and the display further replays the cine image.

2. The ultrasound diagnostic apparatus of claim 1, wherein the image processor is configured to compute a specific value of each image frame stored in the storage and set at least one mark to at least one image frame whose specific value is over a threshold value among the consecutive image frames.

3. The ultrasound diagnostic apparatus of claim 2, wherein the specific value is a mean deviation of each image frame stored in the storage.

4. The ultrasound diagnostic apparatus of claim 1, wherein the storage is configured to store the bookmark information.

5. The ultrasound diagnostic apparatus of claim 1, wherein, if the bookmark setting instruction is not received from the user input device, the image processor is configured to set the bookmarks indicating image frames to be replayed from the storage for display on the display at a constant interval among the consecutive image frames.

6. The ultrasound diagnostic apparatus of claim 5, wherein the image processor is configured to set a plurality of bookmarks to replay the cine image on the display by a plurality of periods.

7. A method of displaying an ultrasound image in ultrasound diagnostic apparatus including a storage, a display, an input device and an image processor, the method comprising:
   a) storing, by the storage, cine data constructed with a plurality of consecutive image frames based on signal processing upon ultrasound echoes from a target object if a real-time display mode is set;
   b) receiving, by the input device, a bookmark setting instruction from a user;
   c) setting bookmarks to a first frame and a last frame of a cine image to be replayed among the consecutive image frames in response to the bookmark setting instruction;
   d) setting, by the image processor, a plurality of marks to a plurality of image frames among the consecutive image frames;
   e) forming, by the image processor, preview images of the image frames with the marks set, the preview images are formed in smaller sizes than the image frames, and the preview images are linked to the corresponding image frames and stored in the storage in association with the corresponding image frames;
   f) if a freeze mode is set from the real-time display mode in response to an instruction inputted from the user input device, reading out the preview images on which the marks are set; displaying the read-out preview images; when a user input for selecting one of the read-out preview images, on which the marks are set, displayed on the display, is received, reading out frame data corresponding to the selected preview image; performing image processing upon the read-out frame data to thereby form a frame image signal, and displaying a frame image based on the frame image signal; and
   g) if a cine replay mode is set from the real-time display mode in response to an instruction inputted from the user input device, reading out preview images on which the bookmarks are set among the preview images on which the marks are set; displaying the read-out preview images and bookmark information including information of the first frame and the last frame of the cine image at the read-out preview images; when a user input for selecting one of the read-out preview images, on which the bookmarks are set, displayed on the display, is received, reading out the frames of the cine image based on the bookmark information; performing image processing upon the frames of the cine image to thereby form the cine image; and replaying the cine image.

8. The method of claim 7, wherein the step d) includes computing a specific value of each image frame, and setting at least one mark to at least one image frame whose specific value is over a threshold value among the consecutive image frames.

9. The method of claim 8, wherein the specific value is a mean deviation of each image frame.

10. The method of claim 7, further including storing the bookmark information.

* * * * *